US00PP34803P2

(12) United States Plant Patent
Thiede

(10) Patent No.: US PP34,803 P2
(45) Date of Patent: Dec. 6, 2022

(54) ***DIANTHUS* PLANT NAMED 'KLEDP20346'**

(50) Latin Name: ***Dianthus caryophyllus* L.**
Varietal Denomination: KLEDP20346

(71) Applicant: Klemm+Sohn GmbH & Co. KG, Stuttgart (DE)

(72) Inventor: Lena Thiede, Riederich (DE)

(73) Assignee: KLEMM+SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 17/744,602

(22) Filed: May 13, 2022

(30) Foreign Application Priority Data

May 20, 2021 (QZ) ..... PBR 20211323

(51) Int. Cl.
*A01H 5/02* (2018.01)
*A01H 6/30* (2018.01)

(52) U.S. Cl.
USPC ..... Plt./277
CPC ..... *A01H 6/305* (2018.05)

(58) Field of Classification Search
USPC ..... Plt./277, 273
CPC ..... A01H 5/02
See application file for complete search history.

(56) References Cited

PUBLICATIONS

CPVO Register Consultation 4.1.68 Citation for 'KLEDP20346'; Jun. 14, 2022; 1 page.*
https://plants.skh.com/12170005/Plant/Print/26500; Jun. 14, 2022; 2 pages.*
https://www.greenleafnursery.com/plant/STROUPERTM-VELVET-WHITE-DIANTHUS-PPAF; Jun. 14, 2022; 1 page.*

* cited by examiner

*Primary Examiner* — Kent L Bell
(74) *Attorney, Agent, or Firm* — Weatherly IP Solutions, LLC; Barbara Campbell

(57) ABSTRACT

A new *Dianthus* plant designated 'KLEDP20346' particularly distinguished by double red-purple flowers having red-purple macules and a compact and upright habit, is disclosed.

1 Drawing Sheet

Genus and species: *Dianthus caryophyllus* L.
Variety denomination: 'KLEDP20346'.

CROSS-REFERENCE TO RELATED APPLICATIONS

This application claims priority to and the benefit of Community Plant Variety Rights Application File No. 2021/1323, filed on May 20, 2021, the entire contents of which are incorporated herein by reference for all purposes.

BACKGROUND OF THE NEW PLANT

The present invention comprises a new and distinct variety of *Dianthus*, botanically known as *caryophyllus* L., and hereinafter referred to by the variety name 'KLEDP20346'. 'KLEDP20346' originated as a naturally-occurring, whole plant mutation from the *Dianthus* parent 'KLEDP07089' (unpatented) in May 2016 in a greenhouse in Stuttgart, Germany.

In August 2016, 'KLEDP20346' was first vegetatively propagated by vegetative stem cuttings in Stuttgart, Germany. 'KLEDP20346' was found to reproduce true to type in successive generations of asexual propagation in Latina, Italy and Stuttgart, Germany via vegetative cuttings.

SUMMARY

The following are the most outstanding and distinguishing characteristics of 'KLEDP20346' when grown under normal horticultural practices in Stuttgart, Germany.

1. Double red-purple flowers having red-purple macules; and
2. An upright and compact plant habit.

DESCRIPTION OF THE PHOTOGRAPH

This new *Dianthus* plant is illustrated by the accompanying photograph of a 13-week-old plant taken in May 2019 and grown in a greenhouse in Stuttgart, Germany. The colors shown are as true as can be reasonably obtained by conventional photographic procedures. The photograph is a whole plant photo of 'KLEDP20346' and shows the foliage, buds, and flowers.

DESCRIPTION

The following detailed descriptions set forth the distinctive characteristics of 'KLEDP20346'. The data which define these characteristics were collected from asexual reproductions carried out in Stuttgart, Germany. Data was collected in March 2022 from plants that were potted in week 41 in 2021 and grown in a greenhouse. Color references are to The R.H.S. Colour Chart of The Royal Horticultural Society of London (R.H.S.), 5$^{th}$ edition (2007).

Classification:
*Family.*—Caryophyllaceae.
*Botanical.*—*Dianthus caryophyllus* L.
*Designation.*—'KLEDP20346'.
*Type.*—Pot carnation.

Parentage: Mutation parent 'KLEDP07089' (unpatented).

Plant:

*Propagation type.*—Vegetative stem cuttings.

*Time to produce a rooted young plant.*—28 days.

*Root description.*—Fine and RHS 155C (White).

*Rooting habit shape.*—Lanceolate.

*Plant form and habit.*—Upright and compact.

*Plant height.*—8.0 cm.

*Plant diameter or spread.*—14.0 cm.

Lateral branches/stems:

*Shape of the branch in cross-section.*—Circular.

*Hollowness of the branch.*—Absent.

*Length.*—8.0 cm.

*Diameter.*—0.2 cm.

*Internode length.*—2.0 cm.

*Internode quantity per branch.*—4.

*Node length.*—0.3 cm.

*Node diameter.*—0.3 cm.

*Texture.*—Smooth.

*Color.*—RHS 137A (Green).

*Flower clustering on the lateral branch.*—In some lateral branches.

Foliage:

*Arrangement.*—Opposite.

*Length.*—5.3 cm.

*Width.*—0.8 cm.

*Shape.*—Obovate.

*Apex.*—Acute.

*Base.*—Obtuse.

*Margin.*—Entire.

*Texture (both upper and lower surfaces).*—Smooth.

*Cross-section of the leaf.*—Moderately concave.

*Curvature of the leaf.*—Absent.

*Glaucosity of the leaf.*—Weak.

*Leaf color (both immature and mature).*—Upper surface: RHS 137A (Green) for immature and RHS N137A (Green) for mature. Lower surface: RHS 137B (Green) for immature and RHS N137D (Green) for mature.

*Venation pattern.*—Absent.

Flowers:

*Flower type and habit.*—Double and round sprays; 2-5 flowers per spray.

*Fragrance.*—Present.

*Position of the flowers compared to the foliage of the plant.*—Same level.

*Profile of both the upper and lower part in the lateral view.*—Flat convex.

*Diameter of the flower.*—4.2 cm.

*Natural flowering season.*—Spring to Autumn.

*Flower longevity on the plant.*—14 days.

Buds:

*Length.*—2.0 cm.

*Diameter.*—1.2 cm.

*Shape.*—Ovate.

*Color.*—RHS 138A (Green).

*Extrusion of the styles at the bud stage.*—Absent.

Corolla:

*Quantity of petals and arrangement.*—24 and arranged in several whorls.

*Corolla height.*—3.0 cm.

*Petal length.*—2.9 cm.

*Petal width.*—1.5 cm.

*Petal shape.*—Obtuse.

*Petal apex.*—Obtuse.

*Petal base.*—Acute.

*Petal margin.*—Crenate.

*Depth of petal margin.*—Shallow.

*Petal texture (both upper and lower surfaces).*—Smooth.

*Petal color.*—Immature: Upper surface: RHS N66A (Red-Purple) with RHS N77A (Purple) macules. Lower surface: RHS 63A (Red-Purple). Mature: Upper surface: RHS 67A (Red-Purple) with RHS 59A (Red-Purple) macules being 0.2 cm in width. Lower surface: RHS 61C (Red-Purple).

*Petal macule quantity.*—1 macule per petal.

*Calyx.*—Quantity of sepals: Composed of 5 sepals. Longitudinal axis of the lobes of the calyx: Straight. Shape: Acute. Calyx height: 2.0 cm. Calyx diameter (at the apex): 1.0 cm. Sepal texture (both upper and lower surfaces): Smooth. Sepal color: Upper surface: RHS 138A (Green). Lower surface: RHS 138C (Green).

*Position of the outer lobes of the epicalyx in relation to the calyx.*—Adpressed.

*Apex shape of the outer lobes of the epicalyx.*—Acute.

*Tip length of the outer lobes of the epicalyx.*—0.5 cm.

*Apex shape of the inner lobes of the epicalyx.*—Short acuminate.

*Tip length of the inner lobes of the epicalyx.*—0.4 cm.

Peduncles:

*Length.*—0.3 cm.

*Diameter.*—0.2 cm.

*Strength.*—Strong.

*Texture.*—Smooth.

*Color.*—RHS 144A (Yellow-Green).

Reproductive organs:

*Stamens.*—Quantity per flower: 4-5. Filament length: 1.0 cm. Filament color: RHS 158D (Yellow-White). Anther length: 0.2 cm. Anther diameter: 0.1 cm. Anther color: RHS 60A (Red-Purple). Pollen amount: None observed to date.

*Pistils.*—Quantity per flower: 4. Length: 1.8 cm. Diameter: 0.4 cm. Stigma: Color: RHS NN155A (White) with RHS 60A (Red-Purple). Shape: Filamentous. Length: 0.1 cm. Diameter: 0.1 cm. Style: Color: RHS 60A (Red-Purple). Length: 0.1 cm. Diameter: 0.1 cm. Ovary: Color: RHS 145B (Yellow-Green). Width: 0.4 cm. Length: 0.9 cm. Shape: Obovate.

Fruit and seed set: None observed to date.

Disease and pest/insect resistance: No disease and pest/insect resistance observed.

COMPARISON OF 'KLEDP20346' WITH PARENTAL LINE AND KNOWN VARIETY

'KLEDP20346' is distinguished from the mutation parent as described in Table 1.

TABLE 1

| Comparison with Parental Line | | |
|---|---|---|
| Characteristic | 'KLEDP20346' | Mutation Parent 'KLEDP07089' |
| Flower color, mature, upper surface | Red-Purple with Red-Purple macules | Cherry red with crimson eyes |

'KLEDP20346' can be compared to the commercial *Dianthus* variety 'KLEDP07088' (Unpatented). Differences between the varieties are described in Table 2.

TABLE 2

| Comparison with Similar Variety | | |
|---|---|---|
| Characteristic | 'KLEDP20346' | 'KLEDP07088' |
| Flower color, mature, upper surface | Red-Purple with Red-Purple macules | Pink with a dark red-purple and white pattern |

TABLE 2-continued

| Comparison with Similar Variety | | |
|---|---|---|
| Characteristic | 'KLEDP20346' | 'KLEDP07088' |
| Growth Habit | Compact Upright and compact | Medium Semi-upright |

I claim:

1. A new and distinct variety of *Dianthus* plant designated 'KLEDP20346' as illustrated and described herein.

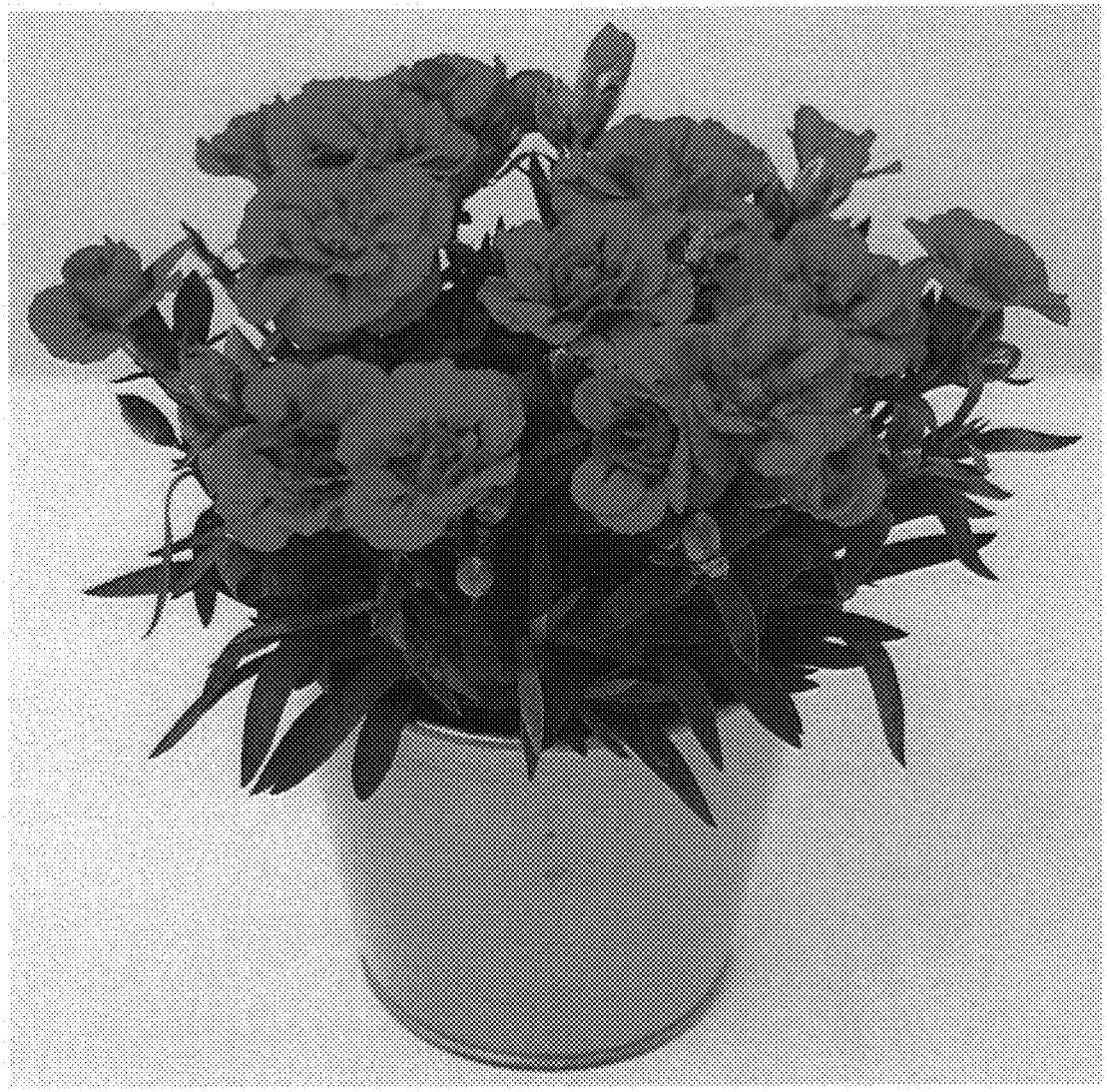

* * * * *